(12) United States Patent
Schmidt et al.

(10) Patent No.: US 6,677,479 B2
(45) Date of Patent: Jan. 13, 2004

(54) SUBSTITUTED FLUOROAROMATICS, PROCESS FOR PREPARING THEM AND THEIR USE

(75) Inventors: Wolfgang Schmidt, Dreieich (DE); Rainer Wingen, Hattersheim (DE)

(73) Assignee: Clariant Finance LBVI Limited (VG)

( * ) Notice: Subject to any disclaimer, the term of this patent is extended or adjusted under 35 U.S.C. 154(b) by 0 days.

(21) Appl. No.: 10/292,036

(22) Filed: Nov. 12, 2002

(65) Prior Publication Data

US 2003/0092930 A1 May 15, 2003

(30) Foreign Application Priority Data

Nov. 13, 2001 (DE) .......................... 101 55 499
Dec. 14, 2001 (DE) .......................... 101 61 611

(51) Int. Cl.[7] .............................................. C07C 65/00
(52) U.S. Cl. ...................... 562/474; 562/853; 562/433; 562/863; 562/861; 562/456; 568/425; 568/437
(58) Field of Search ................. 568/437, 425; 562/853, 433, 863, 861, 456, 474

(56) References Cited

U.S. PATENT DOCUMENTS

| | | | | |
|---|---|---|---|---|
| 3,830,805 A | | 8/1974 | Pilgram ....................... | 260/240 |
| 4,851,160 A | * | 7/1989 | Peterson et al. ............. | 562/853 |
| 5,041,683 A | * | 8/1991 | Marhold et al. ............. | 568/425 |
| 6,482,478 B1 | | 11/2002 | Wingen ....................... | 428/1.1 |
| 2001/0050352 A1 | | 12/2001 | Wingen et al. ............. | 252/299.5 |

FOREIGN PATENT DOCUMENTS

| | | |
|---|---|---|
| DE | 100 22 661 | 11/2001 |
| DE | 101 01 020 | 7/2002 |
| EP | 0 396 987 | 11/1990 |
| EP | 0 612 723 | 8/1994 |
| WO | WO 99/24385 | 5/1999 |

OTHER PUBLICATIONS

English abstract for EP 0612723, Aug. 31, 1994.
English abstract for DE 10101020, Jul. 18, 2002.
Dr. M.J. Monteith, "Recent developments in transition metal catalysed couplings", Specialty Chemicals, Dec. 1998, pp. 436–438.
Kiyoshi Kanie, et al., "A convenient synthesis of trifluoromethyl ethers by oxidative desulfurization–fluorination of dithiocarbonates", Bull. Chem. Soc. Jpn., 73, pp. 471–484 (2000).

* cited by examiner

*Primary Examiner*—Alan L. Rotman
*Assistant Examiner*—Héctor M Reyes
(74) *Attorney, Agent, or Firm*—Alan P. Kass

(57) ABSTRACT

Compounds of the formula (I) and also process for preparing them

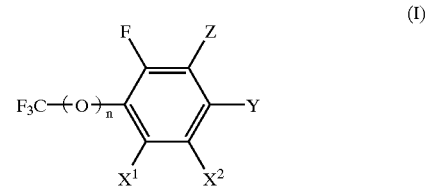

where substituents $X^1$, $X^2$, Y and Z are defined as follows:
$X^1$ is H or F
$X^2$ is H or F
Y is Cl, Br, or I
Z is CHO or COOH or CN
n is 0 or 1 and also their use as starting material for preparing agrochemicals, electronics materials and pharmaceuticals.

20 Claims, No Drawings

SUBSTITUTED FLUOROAROMATICS, PROCESS FOR PREPARING THEM AND THEIR USE

Benzaldehydes and benzoic acids having trifluoromethyl or trifluoromethoxy substituents, with or without additional fluorine substituents, are described extensively in the chemical literature as starting materials for the synthesis of active ingredients (for example U.S. Pat. No. 3,830,805 for aldehydes, EP-A-612 723 for benzoic acids), electronics materials, (JP-A-06 025 120) or generally as intermediates (EP-B-0 396 987).

However, there is a need for trifluoromethyl- and trifluoromethoxybenzaldehydes and benzoic acids having additional functionalities, since these functionalities ease or even make possible introduction into the target structures. The aim of modifying the activity of agrochemicals or pharmaceuticals through fluorination in the form of the trifluoromethyl or trifluoromethoxy group, with or without additional fluorine substituents on the aromatic ring is achieved by varying the lipophilicity and/or the dipolar moment (Kanie et al., Bull. Chem. Soc. Jpn. 2000, 73, 471). It may also be desirable for electronics materials, in particular liquid crystals, to vary the dipolar moment.

The invention accordingly provides compounds of the formula (I)

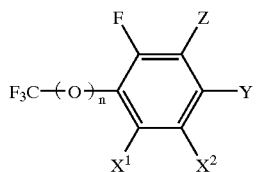

(I)

where substituents $X^1$, $X^2$, Y and Z are defined as follows:
$X^1$ is H or F
$X^2$ is H or F
Y is Cl, Br or I
Z is CHO or COOH or CN
n is 0 or 1
Preference is given to the following compounds in which
a1) $X^1$ and $X^2$: H
   Y: Cl or Br
   Z: CHO
a2) $X^1$ and $X^2$: H
   Y: Cl or Br
   Z: COOH
a3) $X^1$ and $X^2$: H
   Y: Cl or Br
   Z: CN
b1) $X^1$: F $X^2$: H
   Y: Cl or Br
   Z: CHO
b2) $X^1$: F $X^2$: H
   Y: Cl or Br
   Z: COOH
b3) $X^1$: F $X^2$: H
   Y: Cl or Br
   Z: CN
c1) $X^1$ and $X^2$: F
   Y: Cl or Br
   Z: CHO
c2) $X^1$ and $X^2$: F
   Y: Cl or Br
   Z: COOH
c3) $X^1$ and $X^2$: F
   Y: Cl or Br
   Z: CN;
in particular
   2-chloro-6-fluoro-5-trifluoromethylbenzaldehyde
   2-bromo-6-fluoro-5-trifluoromethylbenzaldehyde
   2-chloro-6-fluoro-5-trifluoromethoxybenzaldehyde
   2-bromo-6-fluoro-5-trifluoromethoxybenzaldehyde
   2-chloro-4,6-difluoro-5-trifluoromethylbenzaldehyde
   2-bromo-4,6-difluoro-5-trifluoromethylbenzaldehyde
   2-chloro-4,6-difluoro-5-trifluoromethoxybenzaldehyde
   2-bromo-4,6-difluoro-5-trifluoromethoxybenzaldehyde
   2-chloro-6-fluoro-5-trifluoromethylbenzoic acid
   2-bromo-6-fluoro-5-trifluoromethylbenzoic acid
   2-chloro-6-fluoro-5-trifluoromethoxybenzoic acid
   2-bromo-6-fluoro-5-trifluoromethoxybenzoic acid
   2-chloro-4,6-difluoro-5-trifluoromethylbenzoic acid
   2-bromo-4,6-difluoro-5-trifluoromethylbenzoic acid
   2-chloro-4,6-difluoro-5-trifluoromethoxybenzoic acid
   2-bromo-4,6-difluoro-5-trifluoromethoxybenzoic acid The invention further provides a process for preparing the compounds of the formula (I) where Z=CHO, wherein, a halobenzene of the formula (II) (wherein n, Y, $X^1$ and $X^2$ are each as defined in formula (1) in a solvent or solvent mixture at a temperature which does not support aryne formation is reacted with an organolithium compound. The molar ratio of lithium compound to starting product (II) is preferably 1:1 to 1.2:1. The lithium compound obtained, again at a temperature which does not support aryne formation, is reacted with one formyl equivalent of the formula (III) and then subjected to a hydrolysis to (I). The molar ratio (II):(II) is preferably from 1:1 to 1:2.

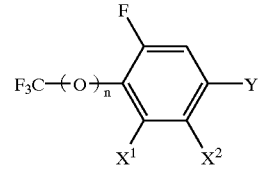

(II)

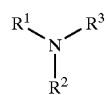

(III)

In (III), $R^1$ is an alkyl radical having from 1 to 6 carbon atoms, a trimethylsilyl radical or an (optionally substituted) phenyl radical, $R^2$ is an alkyl radical having from 1 to 6 carbon atoms, a trimethylsilyl radical or an (optionally substituted) phenyl radical and $R^3$ is —CH(=O) or —CH$(OR^4)_2$; $R^1$ and $R^2$ together with the nitrogen atom may also be part of a five- to seven-membered ring. $R^4$ is an alkyl radical having from 1 to 4 carbon atoms.

Preference is given to reacting (II) with organolithium compounds at a temperature below −60° C., very particular preferably below −70° C., in particular at a temperature in the range from −70° C. to −110° C. The reaction times are in general from 1 to 8 hours. On completion of the reaction (detectable, for example, by TLC or GC), the reaction mixture is gradually heated to −25 to −15° C. and cautiously hydrolyzed using water. The mixture is then acidified using hydrochloric acid to a pH of from 1 to 5 and extracted with a suitable solvent (for example tert-butyl methyl ether, dichloromethane, ethyl acetate, toluene). The extracts of the organic phase are combined and dried, for example, over sodium sulfate). The solvent may be removed under reduced pressure to obtain the desired compound of the formula (I). Any purification required may be effected by chromatography, distillation or crystallization or a combination of the methods mentioned.

The yields are customarily in the range from 50 to 90%, based on (II).

The organolithium compound is preferably the lithium compound of a secondary amine, preferably having sterically demanding substituents. Particular preference is given to lithiumdiisopropylamide, lithium-2,2,6,6-tetramethylpiperidide, lithium dicyclohexylamide, lithium cyclohexylisopropylamide and lithium bis(trimethylsilyl) amide. Very particular preference is given to lithium 2,2,6,6-tetramethylpiperidide and lithium diisopropylamide.

For the compounds of the formula (II) where Y is Cl, the organolithium compound is an alkyllithium compound or the lithium compound of a secondary amine; preference is given to n-butyllithium.

Potassium tert-butoxide may also optionally be added for better activation.

In a preferred embodiment, Y in formula (II) is Br.

It may also be advantageous to add materials to the reaction mixture which activate it or influence the selectivity, for example tetramethylethylenediamine or potassium tert-butoxide (preference is given to the latter in the case of compounds of the formula (II) where Y is Cl).

The formyl equivalent of the formula (III) is preferably N,N-dimethylformamide, N,N-diethylformamide, N,N-dipropylformamide, N,N-diisopropylformamide, N,N-dibutylformamide, N-formylpyrrolidine, N-formylmorpholine, N-formylpiperidine, dimethylformamide dialkyl acetal, N-methylformanilide, N-ethylformanilide or N,N-bis(trimethylsilyl)formamide. The formyl equivalent of the formula (III) is most preferably N,N-dimethylformamide.

For the purposes of the present invention, useful solvents are aprotic solvents, for example ether such as tetrahydrofuran, 1,2-dimethoxyethane, 1,4-dioxane, diethyl ether, or hydrocarbons such as hexane, cyclohexane, heptane, pentane or mixtures of aprotic solvents.

The reaction of (II) with the organolithium compound may also be effected in the presence of the compound (III), so that the lithium derivative of (II) formed in situ can react directly with (III). For this purpose, it may be necessary and advantageous to carry out the reaction above −60° C., for example in the range from −20 to +25° C.

The invention further provides a process for preparing compounds of the formula (I) where Z=COOH, wherein a halobenzene of the formula (II) (where E, Y, $X^1$ and $X^2$ are each as defined above) in a solvent or solvent mixture at a temperature which does not support aryne formation is reacted with an organolithium compound. The molar ratio of lithium compound: starting product (II) is preferably from 1:1 to 1.2:1. The lithium compound obtained, again at a temperature which does not support aryne formation, is reacted with carbon dioxide ($CO_2$) and then subjected to hydrolysis (I).

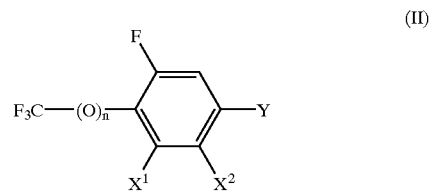

(II)

Preference is given to reacting (II) with the organolithium compound at a temperature below −60° C., very particular preference below −70° C., in particular at a temperature in the range from −70° C. to −110° C. The reaction times are in general from 1 to 8 hours. On completion of the reaction (detectable, for example, by TLC or GC), the reaction mixture is gradually heated to −25 to −15° C. and cautiously hydrolyzed using water. The mixture is then acidified using hydrochloric acid to a pH of from 1 to 5 and extracted with a suitable solvent (for example tert-butyl methyl ether, dichloromethane, ethyl acetate, toluene). The extracts of the organic phase are combined and dried, for example, over sodium sulfate. The solvent may be removed under reduced pressure to obtain the desired compound of the formula (I). Any purification required may be effected by chromatography, distillation or crystallization, precipitation or a combination of the methods mentioned.

The yields are customarily in the range from 50 to 90%, based on (II).

The organolithium compound is preferably the lithium compound of a secondary amine, preferably having sterically demanding substituents. Particular preference is given to lithiumdiisopropylamide, lithium-2,2,6,6-tetramethylpiperidide, lithium dicyclohexylamide, lithium cyclohexylisopropylamide and lithium bis(trimethylsilyl) amide. Very particular preference is given to lithium 2,2,6,6-tetramethylpiperidide and lithium diisopropylamide.

For the compounds of the formula (II) where Y is Cl, the organolithium compound is an alkyllithium compound or the lithium compound of a secondary amine; preference is given to n-butyllithium.

Potassium tert-butoxide may also optionally be used for better activation.

In a preferred embodiment, Y in formula (II) is Br.

It may also be advantageous to add materials to the reaction mixture which activate it or influence the selectivity, for example tetramethylethylenediamine or potassium tert-butoxide (preference is given to the latter in the case of compounds of the formula (II) where Y is Cl).

The carbon dioxide may be added to the reaction mixture on completed metallation in the form of dry ice or the reaction mixture may added to an excess of dry ice. However, it is also possible to pass gaseous carbon dioxide into the reaction mixture, preferably at temperatures above −75° C.

For the purposes of the present invention, useful solvents are aprotic solvents, for example ethers such as tetrahydrofuran, 1,2-dimethoxyethane, 1,4-dioxane, diethyl ether, or hydrocarbons such as hexane, cyclohexane, heptane, pentane or mixtures of aprotic solvents.

The invention further provides the use of compounds of the formula (I) as starting materials for preparing agrochemicals, electronics materials—in particular for components of liquid crystalline mixtures—preferably for fluorinated derivatives of fluorene or phenanthrene—and pharmaceuticals (in particular angiotensin II antagonists).

For this purpose, the compounds of the formula (I) are particularly suitable, since both the aldehyde function (for example by Wittig reaction, reduction to the benzyl alcohol, condensation with C—H—, N—H— or S—H compounds) and the halogen function (which refers here to the function of the substituent Y) (for example by Suzuki coupling, Grignard reaction, Heck reaction) are available for reactions and also—under special conditions in the case of compounds or the subsequent products derived from them in which $X^1$ is F, very particularly in the case of compounds or the subsequent products derived from them in which $X^1$ and $X^2$ are both F—the reactivity of a difluoroaromatic (for example by ortho-metallation) or of a trifluoroaromatic (for example by aromatic nucleophilic substitution) may be utilized.

EXAMPLE 1

2-Bromo-6-fluoro-5-trifluoromethoxybenzaldehyde 400 mmol of 4-bromo-2-fluoro-1-trifluoromethoxybenzene [105529-58-6] are added at −75° C. to a solution of 420 mmol of 2,2,6,6-tetramethylpiperadine and 420 mmol of n-butyllithium (1.6 M solution in n-hexane) in 800 ml of dry tetrahydrofuran. The mixture is left at this temperature for 2 h and then admixed dropwise with 420 mmol of DMF. The reaction mixture is then allowed to gradually thaw, hydrolyzed at −20° C. with water, acidified with hydrochloric acid and extracted with tert-butyl methyl ether. The combined organic extracts are washed with saturated sodium chloride solution and dried over sodium sulfate. After removing the solvent under reduced pressure, the crude product is purified by chromatography on silica gel (eluant: n-heptane/dichloromethane 4:1) and recrystallization from n-heptane. 2-Bromo-6-fluoro-5-trifluoromethoxybenzaldehyde is obtained in the form of slightly yellowish crystals which melt at room temperature. $^1$H-NMR (300 MHz, CDCl$_3$/TMS): δ=7.41 (ddm, $^3J_{HH}$=9 Hz, $^4J_{HF}$=8 HZ $^5J_{HF}$=1 Hz, 1H, H$_{ar}$), 7.54 (dd, $^3J_{HH}$=9 Hz, $^5J$=1.5 Hz, 1H, H$_{ar}$), 10.33 (d, J=1 Hz, 1H, CHO)—$^{19}$F-NMR (282.4 MHz, $^1$H broadband decoupled, CDCl$_3$/CFCl$_3$): δ=−59.36 (d, $^5J_{FF}$=5 Hz, OCF$_3$), −130.23 (q, $^5J_{FF}$=5 Hz, CF).

EXAMPLE 2

2-Chloro-6-fluoro-5-trifluoromethoxybenzaldehyde may be obtained in a similar manner to Example 1 from 4-chloro-2-fluoro-1-trifluoromethoxybenzene [169250-17-3].

EXAMPLE 3

2-Bromo-6-fluoro-5-trifluoromethylbenzaldehyde may be obtained in a similar manner to Example 1 from 4-bromo-2-fluoro-1-trifluoromethylbenzene [142808-15-9].

EXAMPLE 4

2-Bromo-4,6-difluoro-5-trifluoromethylbenzaldehyde may be obtained in a similar manner to Example 1 from 4-bromo-2,6-difluoro-1-trifluoromethylbenzene [156243-64-0].

EXAMPLE 5

2-Bromo-4,6-difluoro-5-trifluoromethoxybenzaldehyde may be obtained in a similar manner to Example 1 from 4-bromo-2,6-difluoro-1-trifluoromethoxybenzene [115467-07-7]. $^1$H-NMR (300 MHz, CDCl$_3$/TMS): δ=8.10 (dd, $^3J_{(HF)}$=10 Hz, $^5J_{(HF)}$=1 Hz, 1H, H$_{ar}$), 10.11 (s, 1 H, CHO)—$^{19}$F-NMR (282.4 MHz, $^1$H broadband decoupled, CDCl$_3$/CFCl$_3$): δ=−58.58 (dd, $^5J_{(FF)}$=7 Hz, OCF$_3$), −116.28 (dq, $^4J_{(FF)}$ and $^5J_{(FF)}$≈7 Hz, CF), −127.90 (dq, $^4J_{(FF)}$ and $^5J_{(FF)}$≈7 Hz, CF).

EXAMPLE 6

2-Chloro-4,6-difluoro-5-trifluoromethoxybenzaldehyde may be obtained in a similar manner to Example 1 from 4-chloro-2,6-difluoro-1-trifluoromethylbenzene [164790-67-4].

EXAMPLE 7

2-Iodo-6-fluoro-5-trifluoromethylbenzaldehyde may be obtained in a similar manner to Example 1 from 4-iodo-2-fluoro-1-trifluoromethylbenzene [239135-53-6].

EXAMPLE 8

2-Bromo-6-fluoro-5-trifluoromethoxybenzoic acid 50 mmol of 4-bromo-2-fluoro-1-trifluoromethoxybenzene [105529-58-6] are added at −75° C. to a solution of 52.5 mmol of diisopropylamine and 52.5 mmol of n-butyllithium (1.6 M solution in n-hexane) in 100 ml of dry tetrahydrofuran. The reaction mixture is left at this temperature for 2 h and then added to dry ice. Hydrolysis is effected using water, acidification with hydrochloric acid and extraction with tert-butyl methylether. The combined organic extracts are washed with saturated sodium chloride solution and dried over sodium sulfate. After removing the solvent under reduced pressure, the crude product is purified by recrystallization from n-heptane. 2-Bromo-6-fluoro-5-trifluoromethoxybenzoic acid is obtained in the form of colorless crystals. Melting point: 112° C. $^1$H NMR (300 MHz, DMSO-d$_6$/TMS): δ=7.67 and 7.71 (overlapping multiplets, 2H)—$^{19}$F NMR (282.4 MHz, $^1$H broadband decoupled, DMSO-d$_6$/CFCl$_3$): δ=−57.6 (d, $^5J_{(FF)}$=5 Hz, OCF$_3$), 129.0 (q, $^5J_{(FF)}$=5 Hz, CF).

EXAMPLE 9

2-Chloro-6-fluoro-5-trifluoromethoxybenzoic acid may be obtained in a similar manner to Example 8 from 4-chloro-2-fluoro-1-trifluoromethoxybenzene [169250-17-3].

EXAMPLE 10

2-Bromo-4,6-difluoro-5-trifluoromethylbenzoic acid may be obtained in a similar manner to Example 8 from 4-bromo-2,6-difluoro-1-trifluoromethylbenzene [156243-64-0].

EXAMPLE 11

2-Bromo-4,6-difluoro-5-trifluoromethoxybenzoic acid may be obtained in a similar manner to Example 8 from 4-bromo-2,6-difluoro-1-trifluoromethoxybenzene [115467-07-7].

EXAMPLE 12

2-Chloro-4,6-difluoro-5-trifluoromethoxybenzoic acid may be obtained in a similar manner to Example 8 from 4-chloro-2,6-difluoro-1-trifluoromethoxybenzene [164790-67-4].

EXAMPLE 13

2-Iodo-6-fluoro-5-trifluoromethylbenzoic acid may be obtained in a similar manner to Example 8 from 4-iodo-2-fluoro-1-trifluoromethylbenzene [239135-53-6].

APPLICATION EXAMPLE 1

A mixture of 98 mmol of 2-bromo-6-fluoro-5-trifluoromethoxybenzaldehyde (Example 1), 112 mmol of 4-pentylphenylboric acid, 225 mmol of cesium fluoride (anhydrous) and 3.4 mmol of tetrakis(triphenylphosphine) palladium(0) in 480 ml of dimethoxyethane is heated to boiling until the reaction is complete. After cooling, the reaction mixture is admixed with tert-butyl methyl ether and water. The organic phase is washed with water and saturated NaCl solution and dried over sodium sulfate, and the solvents are removed under reduced pressure. After chromatographic purification of the crude product (silica gel, heptane/ethyl acetate 9:1), followed by recrystallization from heptane, 3-fluoro-4'-pentyl-4-(trifluoromethoxy)biphenyl-2-carbaldehyde is obtained in the form of colorless crystals. From this, the reaction sequence described in DE-A-101 01 020 (oxidation to the carboxylic acid, conversion to the acid chloride, intramolecular Friedel-Crafts reaction, reduction with triethylsilane) provides 1-fluoro-7-pentyl-2-(trifluoromethoxy)fluorene which, according to DE-A-101 01 020, finds use as a component of nematic or smectic liquid crystal mixtures.

APPLICATION EXAMPLE 2

Compounds of the formula I where Z=CHO may be converted to phenanthrene derivatives in a similar manner to the reaction sequence described in DE-A-100 22 661, by Pd-catalyzed coupling with arylboric acids to give corresponding biphenylcarbaldehydes, Wittig reaction to give (2-methoxy-ethen-1-yl)biphenyls and intramolecular ring closure. In the phenanthrene derivatives, the substitution pattern of trifluoromethyl, trifluoromethoxy and fluoro substituents predefined by (I) recurs. According to WO 99/24385, such phenanthrenes may find use as components of liquid crystalline mixtures.

APPLICATION EXAMPLE 3

Compounds of the formula I where Z=CN prepared from the compounds (I) where Z=COOH by conversion to the carboxamide (for example by reaction with thionyl chloride to the acid chloride; followed by reaction with ammonia; or by conversion to the methyl ester and its reaction with ammonia) with subsequent dehydration to the nitrile (for example using phosphorus pentoxide) may be converted to corresponding biphenylcarbonitriles in a similar manner to the Pd-catalyzed coupling with 4-methylphenylboric acid described in DE-A-100 22 661. In the biphenylcarbonitriles, the substitution pattern of trifluoromethyl, trifluoromethoxy and fluoro substituents predefined by (I) recurs. Such 4-methyl-2'-cyano-biphenyls may be used as starting materials for the synthesis of angiotensin 11 antagonists (see M. J. Monteith, Specialty Chemicals, Dec. 1998, pp. 436–438).

What is claimed is:

1. A compound of the formula (I)

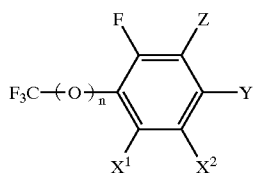

(I)

where substituents $X^1$, $X^2$, Y and Z are defined as follows:
$X^1$ is H or F
$X^2$ is H or F
Y is Cl, Br or I
Z is CHO or COOH or CN
n is 0 or 1.

2. The compound as claimed in claim 1 where:
Z=CHO
a) $X^1$ and $X^2$: H
   Y: Cl or Br or
b) $X^1$:F $X^2$: H
   Y: Cl or Br or
c) $X^1$ and $X^2$: F
   Y: Cl or Br.

3. The compound as claimed in claim 1 where:
Z=COOH
a) $X^1$ and $X^2$: H
   Y: Cl or Br or
b) $X^1$:F $X^2$: H
   Y: Cl or Br or
c) $X^1$ and $X^2$: F
   Y: Cl or Br.

4. A process for preparing a compound as claimed in claim 1 where Z=CHO, wherein a halobenzene of the formula (II), in which n, Y, $X^1$ and $X^2$ are each as defined in claim 1, in a solvent or solvent mixture at a temperature which does not support aryne formation is reacted with an organolithium compound and, afterwards or at the same time, with one formyl equivalent of the formula (III) and then hydrolyzed,

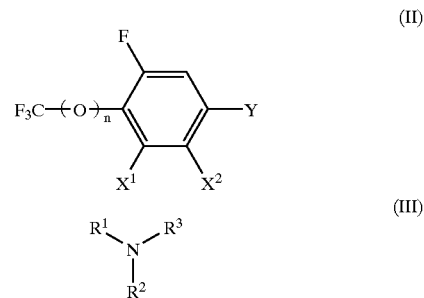

where, in the formula (III), $R^1$ is an alkyl radical having from 1 to 6 carbon atoms, a trimethylsilyl radical or an optionally substituted phenyl radical, $R^2$ is an alkyl radical having from 1 to 6 carbon atoms, a trimethylsilyl radical or an optionally substituted phenyl radical and $R^3$ is —CH(=O) or —CH(OR$^4$)$_2$ where $R^1$ and $R^2$ together with the nitrogen atom may optionally be part of a five- to seven-membered ring and $R^4$ is an alkyl radical having from 1 to 4 carbon atoms.

5. A process for preparing a compound as claimed in claim 1 where Z=COOH, wherein a halobenzene of the formula (II) in a solvent or solvent mixture at a temperature which does not support aryne formation is reacted with an organolithium compound and then with carbon dioxide and subsequent hydrolyzed.

6. The process as claimed in claim 4, wherein the temperature is below −70° C.

7. The process as claimed in claim 4, wherein the compound of the formula (III) is dimethylformamide or diethylformamide.

8. The process as claimed in claim 4, wherein the organolithium compound is lithium 2,2,6,6-tetramethylpiperidide or lithiumdiisopropylamide or, when Y=Cl, is alkyllithium.

9. The process as claimed in claim 4, wherein materials are added to the reaction mixture which activate it or influence the selectivity, in particular tetramethylenediamine or potassium tert-butoxide.

10. The process as claimed in claim 4, wherein the halobenzene of the formula (II) is reacted with the organolithium compound in the presence of the compound of the formula (III).

11. The process as claimed in claim 10, wherein the reaction is carried out at a temperature in the range from −20 to +25° C.

12. A method for preparing agrochemicals, electronics materials and pharmaceuticals comprising using the compound as claimed in claim 1 as a starting material.

13. The method as claimed in claim 12, wherein the electronics materials are components of liquid crystalline mixtures.

14. The method as claimed in claim 13, wherein the components of liquid crystalline mixtures are fluorinated derivatives of fluorene or phenanthrene.

15. A method for preparing agrochemicals, electronics materials and pharmaceuticals comprising using the compound as claimed in claim 2 as a starting material.

16. The method as claimed in claim 15, wherein the electronics materials are components of liquid crystalline mixtures.

17. The method as claimed in claim 15, wherein the components of liquid crystalline mixtures are fluorinated derivatives of fluorene or phenanthrene.

18. A method for preparing agrochemicals, electronics materials and pharmaceuticals comprising using the compound as claimed in claim 3 as a starting material.

19. The method as claimed in claim 18, wherein the electronics materials are components of liquid crystalline mixtures.

20. The method as claimed in claim 18, wherein the components of liquid crystalline mixtures are fluorinated derivatives of fluorene or phenanthrene.

* * * * *